(12) United States Patent
Pai

(10) Patent No.: US 12,127,896 B2
(45) Date of Patent: Oct. 29, 2024

(54) ELECTRONIC IDENTIFICATION BAND FOR OPERATING ROOM INSTRUMENTS

(71) Applicant: RFID INTEGRATED MARKETING CO., LTD., Taichung (TW)

(72) Inventor: Tung-Sheng Pai, Taichung (TW)

(73) Assignee: RFID INTEGRATED MARKETING CO., LTD., Taichung (TW)

( * ) Notice: Subject to any disclaimer, the term of this patent is extended or adjusted under 35 U.S.C. 154(b) by 0 days.

(21) Appl. No.: 18/371,943

(22) Filed: Sep. 22, 2023

(65) Prior Publication Data
US 2024/0108435 A1    Apr. 4, 2024

(30) Foreign Application Priority Data

Sep. 29, 2022   (TW) ................................ 111210605

(51) Int. Cl.
*G06K 19/07*     (2006.01)
*A61B 90/98*     (2016.01)
*G06K 19/077*    (2006.01)

(52) U.S. Cl.
CPC .......... *A61B 90/98* (2016.02); *G06K 19/0723* (2013.01); *G06K 19/0776* (2013.01); *G06K 19/07773* (2013.01)

(58) Field of Classification Search
CPC ............... A61B 90/98; G06K 19/0723; G06K 19/0776; G06K 19/07773

USPC ........................................................ 235/492
See application file for complete search history.

(56) References Cited

U.S. PATENT DOCUMENTS

| | | | |
|---|---|---|---|
| 8,390,452 B2 * | 3/2013 | Blake | A61B 90/98 |
| | | | 40/661.09 |
| 2018/0098822 A1 | 4/2018 | Bilsoe | |
| 2019/0197380 A1 * | 6/2019 | Blank | G06K 19/00 |
| 2019/0290391 A1 | 9/2019 | Liu | |
| 2020/0129267 A1 | 4/2020 | Lento | |

FOREIGN PATENT DOCUMENTS

| | | |
|---|---|---|
| JP | 2014-086020 A | 5/2014 |
| TW | I728995 B | 6/2021 |
| WO | WO2008/062387 A2 | 5/2008 |

* cited by examiner

*Primary Examiner* — Daniel A Hess
(74) *Attorney, Agent, or Firm* — Birch, Stewart, Kolasch & Birch, LLP

(57) ABSTRACT

An electronic identification band can be tightly attached to and surrounded around operating room instruments of various types or specifications for wireless identification by appropriately trimming the length thereof and then peeling off a release paper. The electronic identification band includes a protective housing directly formed on a mounting portion of an elongated flexible substrate to encase an RFID unit therein, such that the RFID unit can be isolated from an ambient environment by a simple structure, thereby achieving the protective function and thus significantly enhancing the economic efficiency in manufacturing the electronic identification band.

9 Claims, 6 Drawing Sheets

ELECTRONIC IDENTIFICATION BAND FOR OPERATING ROOM INSTRUMENTS

BACKGROUND OF THE INVENTION

1. Field of the Invention

The present invention relates generally to an electronic identification band for operating room instruments, which is simple in structure, easy to manufacture, and suitable for operating room instruments of various types and specifications. It is designed to prevent detachment and loss after installation.

2. Description of the Related Art

Nowadays, medical institutions are constantly striving to improve the quality of medical to prevent medical errors. Unfortunately, medical errors are still inevitable. Therefore, patient safety has always been one of the most important issues for the World Health Organization (WHO) and countries in Europe, the United States, Japan, and elsewhere. It is also a critical topic for healthcare service systems in countries around the world.

The operating room is a high-risk, high-cost, complex, professional, and high-tech place. Typically, to perform a surgery, a team composed of surgeons, anesthesiologists, anesthesia nurses, circulating nurses, and other operating room personnels is required. In common medical error cases, 16.9% of surgical adverse events occur due to medical negligence. To reduce medical errors and negligence, and improve patient safety in the operating room, it is crucial to have pre-surgery sterilization and checking on suppled instruments, supervision of instrument usage during surgery, and post-surgery instrument recovery, sorting, inventory, and sterilization. Using RFID (Radio-Frequency Identification) technology to identify operating room instruments should bring safety and efficiency to the aforesaid tasks. Especially, by means of identifying and tracking the instruments before and after use in surgery, hospitals can ensure thorough and complete sterilization, thereby avoiding the risk of hospital-acquired infections or preventing the incidents that the operating room instruments are left inside the human body.

Commercially available RFID tags are typically adhered to instruments by adhesive, resulting in that they may be easily lost during the cleaning and sterilization process. If these tags are applied to metallic instruments, an issue that metal interferences communication may be arisen.

Taiwan patent publication No. TW 202226261A discloses an electronic identifier for operating room instruments. Although the aforesaid disclosure may address the above-mentioned disadvantages, the fixed diameter (size) of the telescope strap that wraps around the instrument cannot be adjusted. This limitation affects the applicability to various instruments. Further, in the process of forming/making the base, male and female fasteners must be embedded in the forming mold in advance. This meticulous and time-consuming process significantly affects the product cost and manufacturing efficiency of the electronic identifier.

SUMMARY OF THE INVENTION

The present invention has been accomplished in view of the above-noted circumstances. It is an objective of the present invention to provide an electronic identification band for an operating room instrument, which can tightly fix an RFID unit to the operating room instrument to prevent the RFID unit from loss during cleaning and sterilization process.

To attain the above-mentioned objective, the present invention provides an electronic identification band for an operating room instrument, which comprises an elongated flexible substrate, a radio-frequency identification (RFID) unit, a protective housing, and a back adhesive layer. The elongated flexible substrate is a flexible insulating soft plastic sheet having a mounting portion. The RFID unit is mounted on the elongated flexible substrate. The protective housing is formed on a top surface of the mounting portion of the elongated flexible substrate at a place surrounding the RFID unit in a way that the protective housing covers the RFID unit to isolate the RFID unit from an ambient environment. The back adhesive layer is provided at a bottom surface of the elongated flexible substrate.

With the above-described technical features, the electronic identification band can be tightly attached to and surrounded around operating room instruments of various types or specifications for wireless identification by means of appropriately trimming the length of the elongated flexible substrate and peeling off a release paper optionally provided at a bottom surface of the back adhesive layer, thereby preventing the RFID unit of the electronic identification band from loss during cleaning and sterilization process. Further, the protective housing is directly formed on the mounting portion of the elongated flexible substrate to encase the RFID unit therein, such that the RFID unit can be isolated from an ambient environment by a simple structure, thereby achieving the protective function and significantly enhancing the economic efficiency in manufacturing the electronic identification band.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE INVENTION

Figure 1:
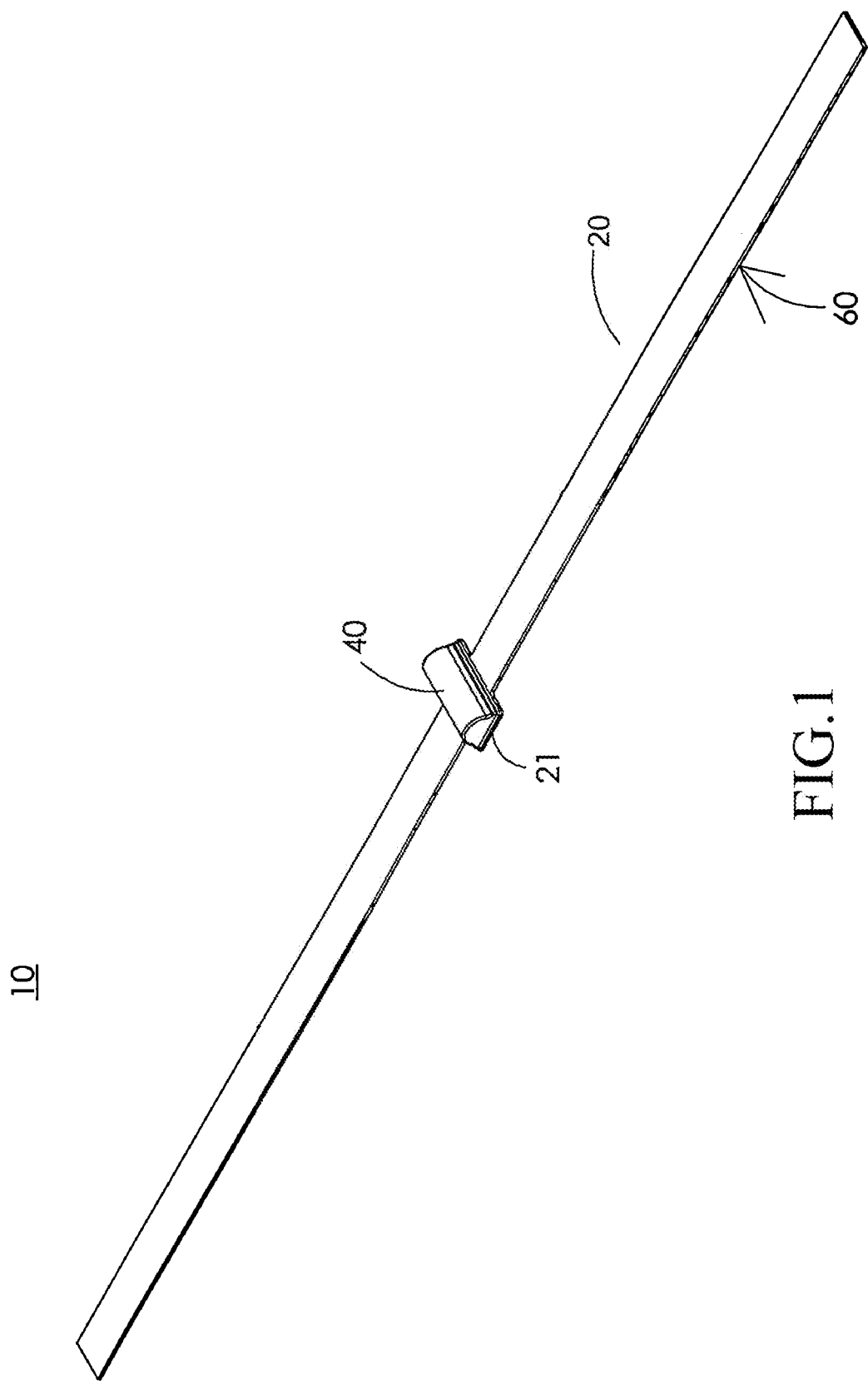
FIG. 1 is a perspective view of an electronic identification band in accordance with an embodiment of the present invention.

Hereunder an embodiment will be detailedly described with accompanying drawings for illustrating technical features and structure of the present invention. As shown in FIGS. 1-4, an electronic identification band 10 for an operating room instrument 70, which is provided in accordance with an embodiment of the present invention, comprises an elongated flexible substrate 20, a radio-frequency identification (hereinafter referred to as "RFID") unit 30, a protective housing 40, a back adhesive layer 50, and a release paper 60.

The elongated flexible substrate 20 is a flexible insulating soft plastic substrate sheet having a mounting portion 21. On the top surface of the mounting portion 21, a mounting piece 22 made of a metal foil, e.g., made by etching a copper foil, is provided.

The RFID unit 30 is attached on the mounting piece 22 of the elongated flexible substrate 20.

The protective housing 40 is directly molded onto the top surface of the mounting portion 21 of the elongated flexible substrate 20 at a place surrounding the RFID unit 30 in such a way that the protective housing 40 covers the RFID unit 30 to isolate the RFID unit 30 from an ambient environment.

The back adhesive layer 50 is coated on the bottom surface of the elongated flexible substrate 20.

The release paper 60 is adhered to the bottom surface of the back adhesive layer 50 to prevent the back adhesive layer 50 from sticking to foreign objects during normal use.

Figure 4:
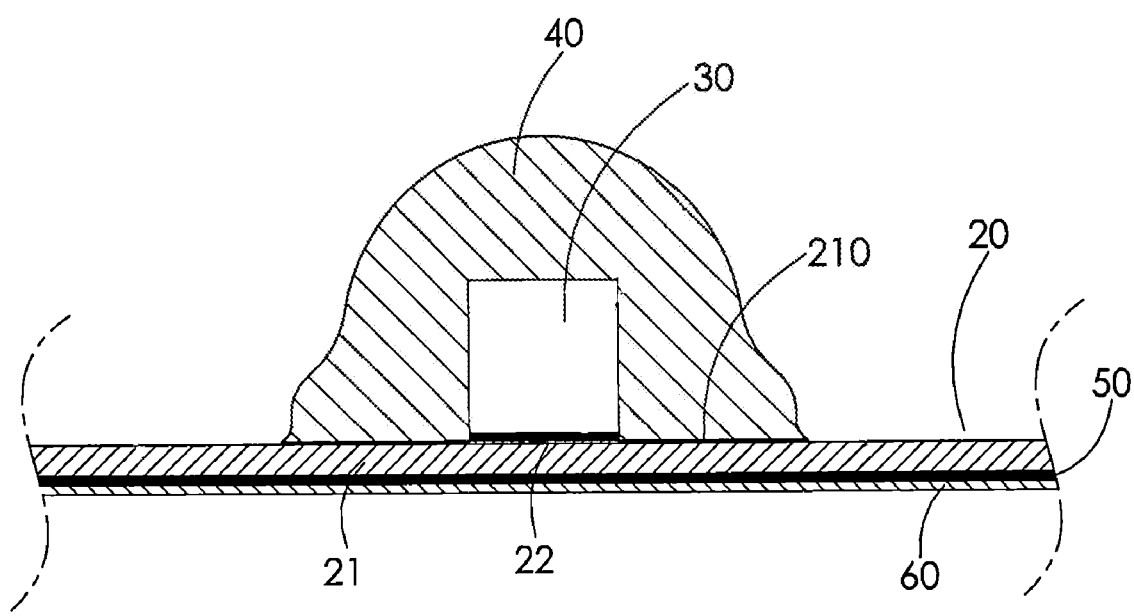
FIG. 4 is a partially cross-sectional view of the electronic identification band of the embodiment of the present invention.
Figure 5:
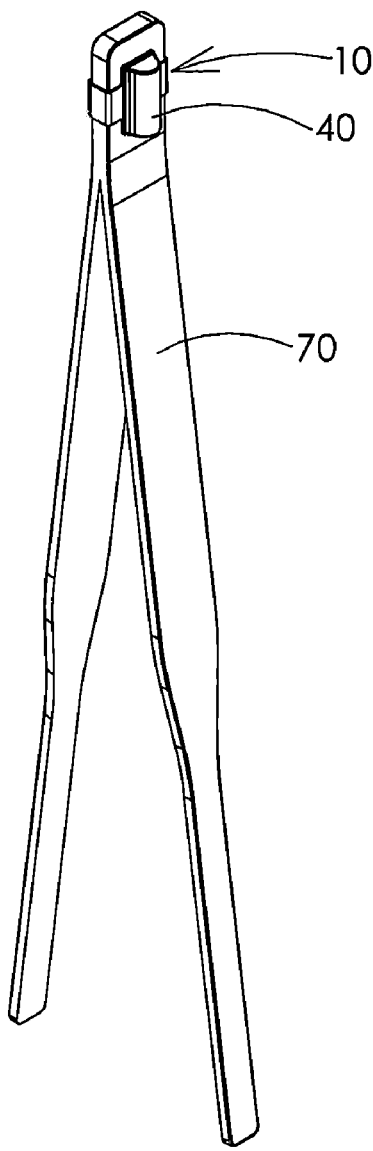
FIG. 5 is a perspective view showing that the electronic identification band is fixed to an operating room instrument.
Figure 6:
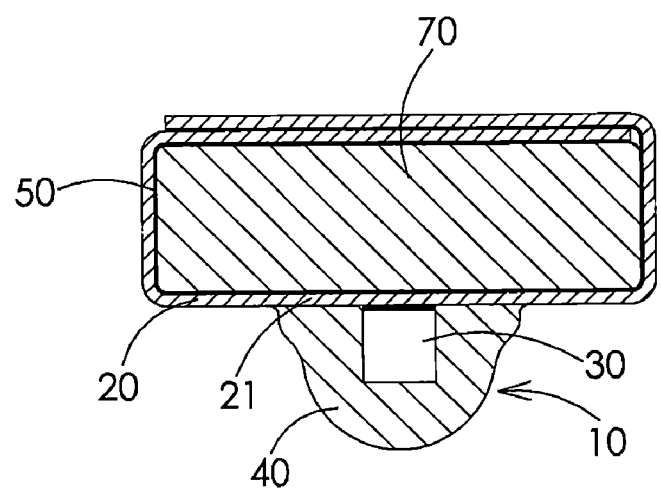
FIG. 6 is a partially cross-sectional view of FIG. 5.

As shown in FIGS. 1, 5, and 6, to fix the electronic identification band 10 to an operating room instrument 70, it is only necessary to trim the length of the elongated flexible substrate 20 (including release paper 60) appropriately, and then peel off the release paper 60, and thereafter attach and wrap the electronic identification band 10 around the operating room instrument 70. As such, the electronic identification band 10 can be tightly attached to and wrapped around the operating room instrument 70 of various types or specifications for wireless identification, thereby preventing the RFID unit 30 of the electronic identification band 10 from loss during cleaning and sterilization process. As shown in FIGS. 1 and 4, the protective housing 40 is directly formed on the mounting portion 21 of the elongated flexible substrate 20 to encase the RFID unit 30 therein, such that the RFID unit 30 can be isolated from an ambient environment by a simple structure, thereby achieving the protective function and significantly enhancing the economic efficiency in manufacturing the electronic identification band 10.

Figure 2:
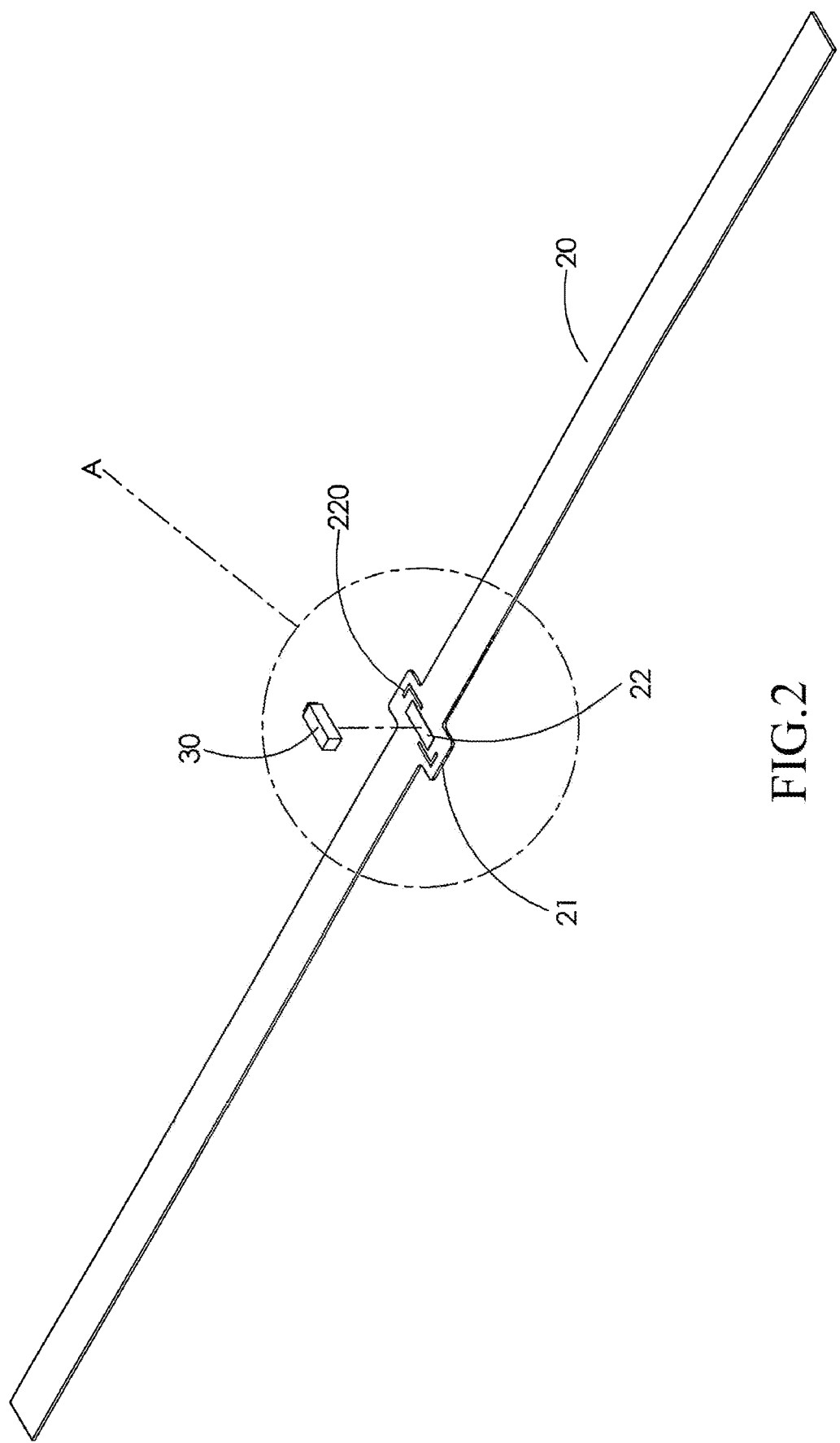
FIG. 2 is an exploded perspective view, showing an elongated flexible substrate and an RFID unit.

In accordance with the above embodiment, as shown FIGS. 1 and 2, the elongated flexible substrate 20 may be made of a flexible polyimide (PI) sheet. As illustrated in FIGS. 5 and 6, when the electronic identification band 10 is used on an operating room instrument 70, the electronic identification band 10 can undergo high-temperature sterilization along with the operating room instrument 70 thanks to the high temperature withstanding characteristic of the material of the elongated flexible substrate 20.

In accordance with the above embodiment, as shown in FIGS. 1 and 2, on the top surface of the mounting portion 21 of the elongated flexible substrate 20, a location-identifying mark 220 (in the form of double brackets in this embodiment) can be further provided around an outer periphery of the mounting piece 22. The location-identifying mark 220 is used to indicate the position of the mounting piece 22, facilitating the application of adhesive or solder paste onto the mounting piece 22 for attaching the RFID unit 30 thereon by a way of surface mount technology (SMT) for example.

Figure 3:
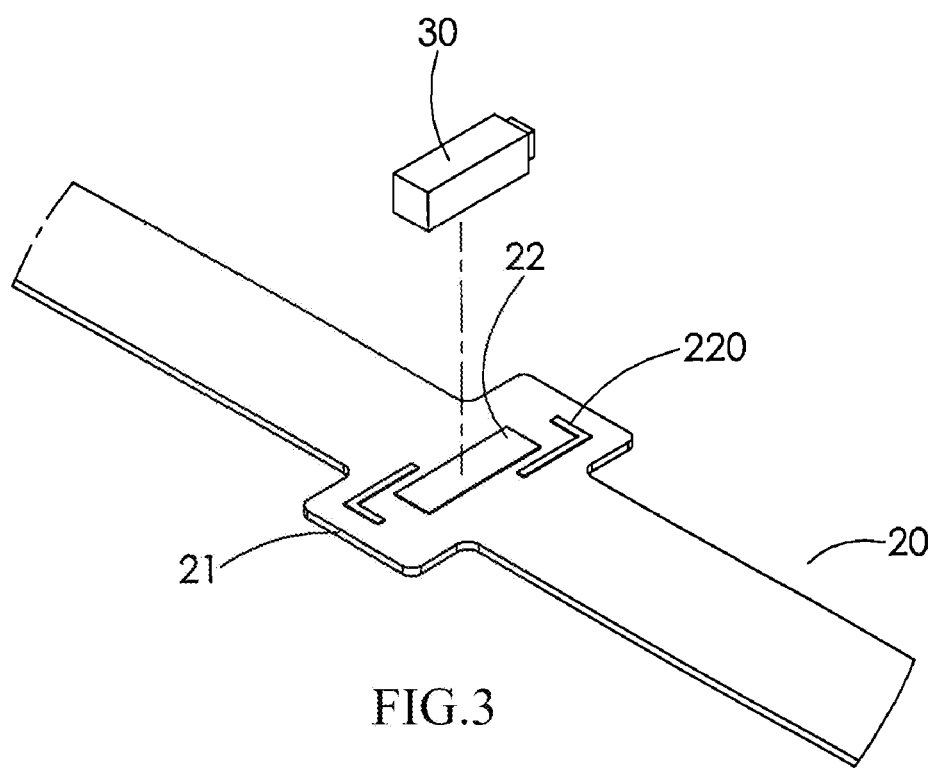
FIG. 3 is an enlarged view of the part A of FIG. 2.

In accordance with the above embodiment, as shown in FIGS. 2, 3, and 4, at a place of the top surface of the mounting portion 21 surrounding the RFID unit 30, an adhesive layer 210 may be applied first. The adhesive layer 210 contains an adhesive matrix and a crosslink agent having functional groups that can be crosslinked to the adhesive matrix and the material of the protective housing 40. When the protective housing 40 is formed on the place of the top surface of the mounting portion 21 surrounding the RFID unit 30, the functional groups of the crosslinking agent enable a crosslinking effect between the adhesive layer 210 and the protective casing 40, ensuring a secure attachment of the protective housing 40 to the top surface of the mounting portion 21. Furthermore, the material of the protective housing 40 may be silicone, silicone rubber, or a combination thereof, and the adhesive matrix contains thermoplastic material. These technical features allow the electronic identification band 10, when it is used on an operating room instrument 70, to achieve a good isolating and protective effect to the RFID unit 30 during the cleaning and sterilization process of the operating room instrument 70 because the high-temperature and chemically resistant protective housing is tightly bonded on the mounting portion 21 of the elongated flexible substrate 20 and covers over the RFID unit 30, as shown in FIGS. 1, and 5-6. Moreover, in manufacture of the electronic identification band 10, the elongated flexible substrate 20 can be placed in a heat-press forming mold (not shown) first, and then the silicone or silicone rubber material is applied on the top surface of the mounting portion 21 of the elongated flexible substrate 20 and then thermally pressed by the forming mold to form the protective housing 40 at the place of the top surface of the mounting portion 21 surrounding the RFID unit 30. Alternatively, in manufacture of the electronic identification band 10, the elongated flexible substrate 20 can be placed in an injection mold (not shown) first. Thereafter, the protective housing 40 at the place of the top surface of the mounting portion 21 surrounding the RFID unit 30 can be formed by injecting silicone or silicone rubber material into the injection mold by using an injection machine.

According to the above embodiment, the RFID unit 30 may be an anti-metal ultra-high frequency radio frequency identification (UHF RFID) tag having a built-in ceramic antenna. This allows an electronic reading device (not shown) to achieve a long-distance reading of the ID code of the RFID unit 30 equipped in the electronic identification band 10 that is installed on the metallic operating room instrument 70. Taking a UHF RFID system using a frequency range of 922 MHz to 928 MHz and planned for hospitals for example, when the electronic identification band 10 is installed on a metallic operating room instrument 70, as shown in FIG. 5, the theoretical reading distance measured through a reading distance test is approximately 0.76 to 0.81 meters. This confirms that the electronic identification band 10, which is used on the metallic operating room instrument 70, is not affected by metal interference. Moreover, according to the fact that the actual reading distance is about 1.5 times the theoretical reading distance in average, the reading distance of the above electronic identification band 10 used on the operating room instrument 70 will reach about 1.14 to 1.21 meters at the frequency range of 922 MHz to 928 MHz, meeting the requirements of wireless identification management for hospital instruments.

Based on the above-mentioned technical features, various modifications to the structure of the electronic identification band 10 may be made. For example, a high-frequency radio frequency identification (HF RFID) tag may be used as the RFID unit 30. Further, the mounting piece 22 may be omitted, and the RFID unit 30 may be directly attached to the mounting portion 21 of the elongated flexible substrate 20 by using adhesives, such as UV-curing adhesive. Furthermore, the release paper 60 may also be omitted, and in this case, after the adhesive layer 50 is applied to the elongated flexible substrate 20, it can be attached to the operating room instrument 70 directly. Such variations are not to be regarded as a departure from the scope of the invention, and all such modifications as would be obvious to one skilled in the art are intended to be included within the scope of the following claims.

What is claimed is:

1. An electronic identification band for an operating room instrument, comprising:
   an elongated flexible substrate, which is a flexible insulating soft plastic sheet having a mounting portion;
   a radio-frequency identification (RFID) unit mounted on the elongated flexible substrate, wherein the RFID unit is an anti-metal RFID tag having a built-in ceramic antenna;
   a protective housing formed on a top surface of the mounting portion of the elongated flexible substrate at a place surrounding the RFID unit in a way that the protective housing covers the RFID unit to isolate the RFID unit from an ambient environment; and
   a back adhesive layer provided at a bottom surface of the elongated flexible substrate.

2. The electronic identification band as claimed in claim 1, wherein the elongated flexible substrate is made of a flexible polyimide sheet.

3. The electronic identification band as claimed in claim 1, wherein the mounting portion of the elongated flexible substrate is provided at the top surface thereof with a mounting piece and a location-identifying mark around an outer periphery of the mounting piece.

4. The electronic identification band as claimed in claim 1, wherein at the place of the top surface of the mounting portion surrounding the RFID unit, an adhesive layer is provided in a way that the adhesive layer comprises an adhesive matrix and a crosslinking agent having functional groups crosslinked with the adhesive matrix and a material of the protective housing.

5. The electronic identification band as claimed in claim 4, wherein the material of the protective housing is selected from a group consisting of silicone, silicon rubber, and a combination thereof; the adhesive matrix of the adhesive layer comprises thermoplastic material.

6. The electronic identification band as claimed in claim 5, wherein the material of the protective housing is applied on the top surface of the mounting portion of the elongated flexible substrate and then thermally pressed by a mold to form the protective housing at the place of the top surface of the mounting portion surrounding the RFID unit.

7. The electronic identification band as claimed in claim 5, wherein the material of the protective housing is injected into a mold, in which the elongated flexible substrate is placed, to form the protective housing at the place of the top surface of the mounting portion surrounding the RFID unit.

8. The electronic identification band as claimed in claim 1, wherein the top surface of the mounting portion is disposed with a mounting piece of metal foil, on which the RFID unit is mounted.

9. The electronic identification band as claimed in claim 1, further comprising a release paper attached to a bottom surface of the back adhesive layer.

* * * * *